(12) United States Patent
Koster et al.

(10) Patent No.: US 8,788,679 B2
(45) Date of Patent: Jul. 22, 2014

(54) METHOD FOR EXCHANGING DATA

(75) Inventors: Robert P. Koster, Eindhoven (NL); Milan Petkovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 205 days.

(21) Appl. No.: 13/141,170

(22) PCT Filed: Dec. 15, 2009

(86) PCT No.: PCT/IB2009/055759
§ 371 (c)(1),
(2), (4) Date: Jun. 21, 2011

(87) PCT Pub. No.: WO2010/073183
PCT Pub. Date: Jul. 1, 2010

(65) Prior Publication Data
US 2011/0264809 A1    Oct. 27, 2011

(30) Foreign Application Priority Data
Dec. 22, 2008 (EP) ................................ 08172594

(51) Int. Cl.
*G06F 15/16*    (2006.01)

(52) U.S. Cl.
USPC ............................ 709/227; 709/219

(58) Field of Classification Search
USPC ........................................... 709/227
See application file for complete search history.

(56) References Cited

U.S. PATENT DOCUMENTS

| | | | |
|---|---|---|---|
| 5,245,656 A | 9/1993 | Loeb et al. | |
| 2004/0215824 A1* | 10/2004 | Payrits | 709/245 |
| 2006/0129816 A1* | 6/2006 | Hinton | 713/169 |
| 2007/0027715 A1* | 2/2007 | Gropper et al. | 705/2 |
| 2008/0046292 A1 | 2/2008 | Myers et al. | |

FOREIGN PATENT DOCUMENTS

| | | |
|---|---|---|
| GB | 2403041 A | 12/2004 |
| JP | 2003186997 A | 7/2003 |
| JP | 2003308386 A | 10/2003 |
| WO | 0065522 A2 | 11/2000 |
| WO | 0190968 A1 | 11/2001 |
| WO | 2008147566 A1 | 12/2008 |

OTHER PUBLICATIONS

Chivers, H.; Grid Security: Problems and Potential Solutions; 2003; Report—University of York Department of Computer Science; 7 pages.

(Continued)

*Primary Examiner* — John B. Walsh

(57) ABSTRACT

The present invention relates to a method for exchanging data between at least two servers with use of a gateway. Preferably the method is applied to healthcare systems. Each server holds a unique federated identifier, which identifier identifies a single patient (P). Thus, it is possible for the servers to communicate with each other without having to reveal the true identity of patient. By creating one session pseudonym for each pair of providing server (12) holding relevant patient data and a requesting server (10) and by formatting an inbound session identifier related to the requesting server and an outbound session identifier related to the providing server for each session pseudonym the servers may communicate anonymous data with each other. The patient data is transferred from the at least one providing server to the requesting server and all session pseudonyms are replaced, in the requesting server, with the identifier of the requesting server for the patient (P).

20 Claims, 3 Drawing Sheets

(56) References Cited

OTHER PUBLICATIONS

Girao, J., et al.; A Practical Approach to provide Communication Privacy; 2006; IEEE Int'l Conf. on Communications; vol. 5:1965-1970.

Pfitzmann, A., et al.; Anonymity, Unlinkability, Undetectability, Unovservability, Pseudonymity;and Identity Management—A Consolidated Proposal for Terminology; [online] Feb. 15, 2008; http://dud.inf.tu-dresden.de/literatur/Anon_Terminology_v0.31.pdf.

Pommerening, K., et al.; Secondary Use of the EHR via Pseudonymisation; 2004; Studies in Health Technology and Informatics; vol. 103; pp. 441-446.

"Data Security", Sonablate International HIFU Registry.

* cited by examiner

METHOD FOR EXCHANGING DATA

TECHNICAL FIELD OF THE INVENTION

This invention relates to a method for exchanging data between at least two severs with the use of a gateway.

DESCRIPTION OF RELATED ART

In many applications a central party acts as a gateway when data is exchanged between different servers in a network. Examples include Personal Health Record (PHR) architectures, such as e.g. WebMD, DOSSIA, Microsoft HealthVault, Electronic Health Record (EHR) architectures, e.g. NICTIZ in the Netherlands and Infoway in Canada, and web-services for e.g. e-commerce. Gateways may just relay data or aggregate data, which is the case in a typical PHR or EHR application. Another use of gateways involves them just as a reference index to resolve identifiers without directly relaying or aggregating data.

A special circumstance when it comes to all kinds of medical records is that it is necessary to preserve the patient anonymity and linkability when exchanging information between different servers. This is of course also true for other systems that want to un-identify certain data during exchange between different servers.

These applications typically use a concept called federated identity management, often by adopting standards like SAML, Liberty Alliance or WS-Federation. This means that each party holds its own identifier, and other identity information, for the same object, such as a patient or a customer. These identifiers are logically linked—federated—at an intermediate gateway service provider, which may be an EHR, an e-commerce gateway etc.

Identity Federation Framework (ID-FF) is a standard created by the Liberty Alliance Project to enable identity federation between multiple enterprises via web services. The Liberty Alliance Federation Framework architecture provides a pseudonym-based solution, which uses pseudonyms as the keys to link federated accounts between enterprises, so that one enterprise does not need to know the actual identifier of a user at another enterprise. This, along with support for pseudonyms, enables the construction of flexible federations that can adhere to privacy laws and regulations as well as privacy decisions of individual user.

In the Liberty alliance solution, the gateway has typically the role of identity administrator, whereas a requesting server and a providing server have a service render role.

The document "Connecting for health" at http://www.connectingforhealth.org/resources/final_phwg_report1.pdf describes a typical PHR application where an intermediary gateway helps to collect and organize the personal health information in the PHR. This architecture allows exchange of data into and out of the PHR. There are two major variations of this model.

In the Independent Vendor Integration model, a sponsor establishes a central database through which PHR data is transmitted from data sources (doctor's office, pharmacy, lab etc.) to the PHR and vice versa. PHR reports could be generated on demand or automatically at specified intervals from the central database for use by the individual user and, with permission, for use by providers and other trusted entities (e.g., child's school, pharmacy, specialist etc.). This model makes it easy to collect data from a variety of sources on behalf of an individual. This model might be easier for people to use since they would not have to establish and maintain the PHR on their own. However, there are concerns about the security of personal health information and the mechanics of enabling user control of all information releases. Additional research would be needed regarding people's trust and acceptance of a third party sponsored system. Providers would need to have the capacity to interface with the system using community wide data standards or by means of "translation" protocol operated by the vendor.

An alternative to the Independent Vendor Integration model is to establish a repository of identifying information about an individual, rather than a centralized personal health information database, and a system to map the identifiers to all of the associated data sources in the community. In this model, reports are generated on demand, or at specified intervals, but the linked data is not retained in the system. The model has similar advantages in terms of consumer ease of access and use. Provider systems requirements are minimized since data is retrieved in whatever forms it currently exists. The application of clinical decision support tools and real-time analytical protocols across this distributed data environment could be cumbersome, and the compilation of longitudinal data would require each data supplier to follow common archiving protocols.

A problem with known anonymization architectures is that they induce high processing load on the gateway, which must repeatedly resolve and replace pseudonyms. Since, most EHR solutions are based on standards like HL7, which use XML for data interchange, this is a heavy task, especially if the pseudonyms are located at arbitrary places within the XML documents. Most processing time in web-services is spent on decoding and processing XML structures.

Hence an improved method for exchanging data allowing for increased efficiency and preserved privacy would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems by providing a method for exchanging data according to the appended patent claims.

An object according to some embodiments is to provide an efficient method for exchanging data between at least two servers while preserving privacy.

This problem is solved by a method for exchanging data between at least two servers with use of a gateway, wherein each server holds a unique federated identifier, which identifier identifies a single patient. Each sever may act both as a requesting server or providing server. The method comprises the following steps; sending an original request requesting data of the patient from the requesting server to the gateway; resolving federated identities with use of the gateway; creating, by the gateway, one session pseudonym for each pair of providing server holding relevant patient data and the requesting server; formatting an inbound identifier array related to the requesting server and an outbound identifier array related to the providing server for each session pseudonym; relaying the identifier arrays to each server, respectively; replacing, by each providing server, the identifier of the patient with the outbound identifier array; transferring the patient data from the at least one providing server to the requesting server; replacing, in the requesting server, all session pseudonyms with the identifier of the requesting server for the patient.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION OF EMBODIMENTS

Figure 1:
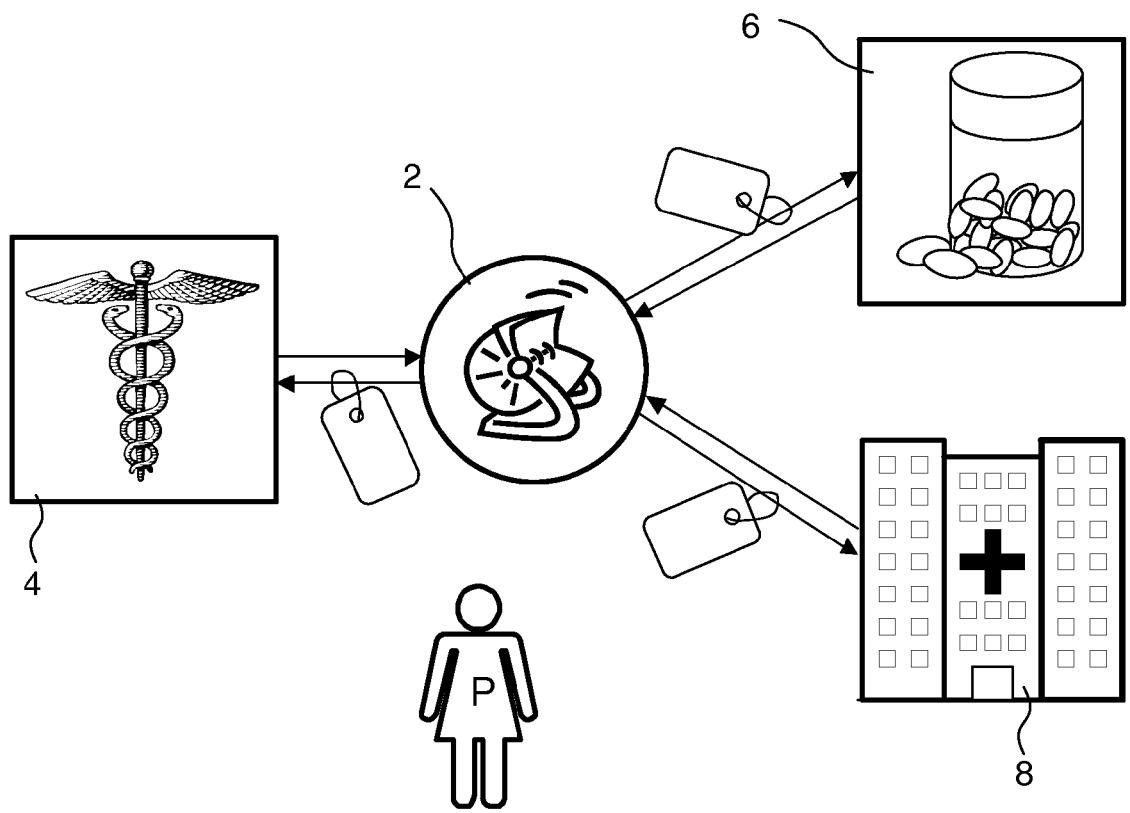
FIG. 1 shows how users of different EMR systems are connected to each other via a gateway server.

FIG. 1 shows an EHR system built up of users having individual Electronic Medical Record (EMR) systems connected to each other via a gateway server 2. The users in FIG. 1 are a general practitioner (GP) 4, a pharmacy 6 and a specialist hospital 8. FIG. 1 further shows a patient P, whose medical records might be stored in some or all of the EMR systems. The EMR systems might be of the same type for all users, but are usually of different types. Regardless of which, each EMR system has its own identifier for the patient P. The gateway server 2 is able to resolve all existing federated identifiers by keeping a register thereof.

A first embodiment of a method will now be described in detail with reference to FIG. 2. This embodiment will be described in conjunction with an electronic health record (EHR) system. However, it can be used in any server-gateway system where each server holds a unique federated identifier for the same single patient.

An EHR refers to one medical record of one individual person in digital format. EHR systems co-ordinate computer-aided storage and retrieval of individual EHRs. EHRs are made up of electronic medical records (EMRs) from many providers. A variety of types of healthcare-related information may be stored and accessed in this way.

When an end-user, who can be the general practitioner (GP), a dentist, a pharmaceutical chemist, or indeed the patient P e.g., requests certain data about patient P, the local EMR server composes a request comprising the local federated identifier of patient P. The request may additionally comprise a specification of the desired type of data wanted. A dentist is likely to be more interested in dental records than immunization records. It should be noted that even if the request may contain a request for certain data it is not given that the data is accessible, due to access control settings. The request may further comprise other suitable parameters applicable to the implementation of the method.

Figure 2:
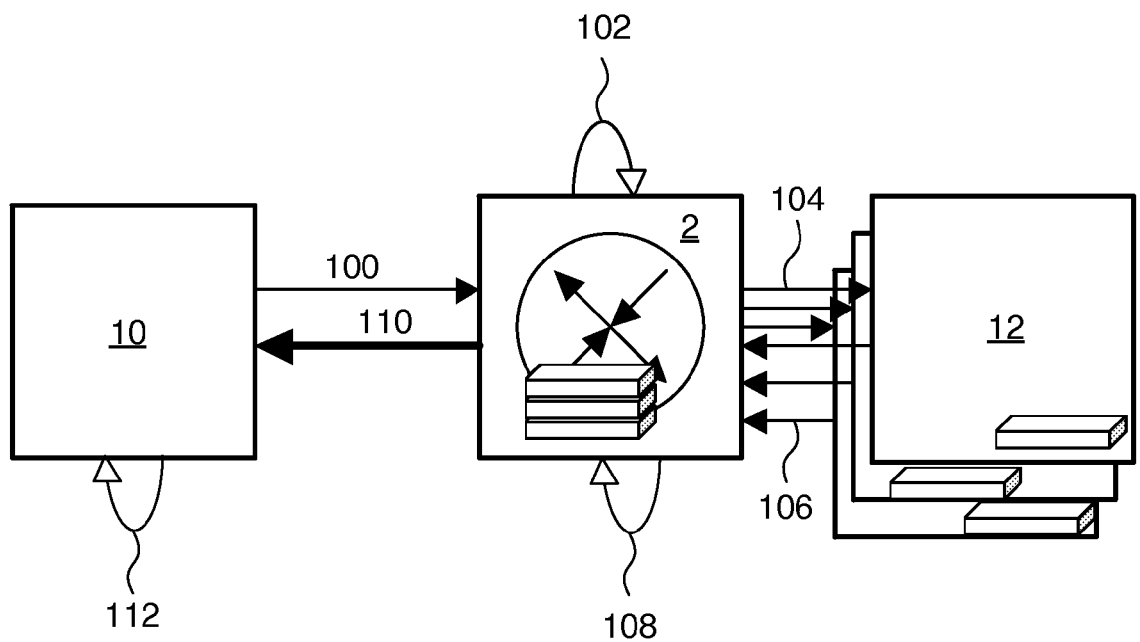
FIG. 2 shows the different steps of a first embodiment of the method according to the present invention.

According to one embodiment of the method the local EMR server is called and acts as a requesting server, which is denoted 10 in FIG. 2. FIG. 2 furthermore shows the gateway 2 and three providing servers 12, which correspond to the EMR systems of the different providers that hold the requested data.

In another embodiment the requesting server may instead be an internal PC connected to the providing servers.

Either way, the request is sent, indicated by arrow 100, to the EHR system gateway 2, which resolves the federated identities related to the patient P and creates, see arrow 102, one session pseudonym for each pair of providing server 12 holding relevant patient data and requesting server 10.

Thereafter the gateway 2 formats an inbound identifier array for the patient P related to the requesting server and an outbound identifier array for the patient P related to the providing server for each session pseudonym. Thus, each session pseudonym is paired with the patient identifier for the requesting server and included in the inbound identifier array for the requesting server and paired with the patient identifier for the providing server and included in the outbound identifier array for the providing server. For each providing server 12 the gateway 2 then prepares an outbound request comprising the respective session pseudonym. It should also be noted that the original identifier of the requesting server is replaced with the session pseudonym. Furthermore, the gateway 2 appends the respective outbound identifier array and relays each request, arrows 104, to each providing server 12, respectively.

Upon reception of a request, the providing server 12 uses the appended outbound identifier array to extract the session pseudonym from the request and select the corresponding identifier for the providing server 12. Furthermore, the providing server retrieves the requested data and sends it back, arrows 106, to the gateway 2 in a response comprising a reference to the session pseudonym, but without any reference to the identifier for the providing server 12.

The gateway 2 awaits all response data prompted by the original request and aggregates it into one response, indicated by arrow 108. Thereafter it appends the inbound identifier array to the response, and relays it back, see arrow 110, to the requesting server 10. The requesting server 10 consequently replaces, see arrow 112, all session pseudonyms with the original identifier before processing the EMR of the patient P, e.g. displaying it to the end-user who originally requested the data.

In a variation of this embodiment, the gateway 2 appends the inbound identifier array to the response and relays it directly to the requesting server 2. The requesting server 2 then makes the aggregation into one response instead of the gateway 2. This embodiment moves more processing tasks away from the gateway 2, and furthermore offers the advantage of architecture flexibility. You may for instance offer functionality which assesses the processing complexity of aggregating and sending one large data record against appending inbound identifier arrays to and sending many small data records.

Figure 3:
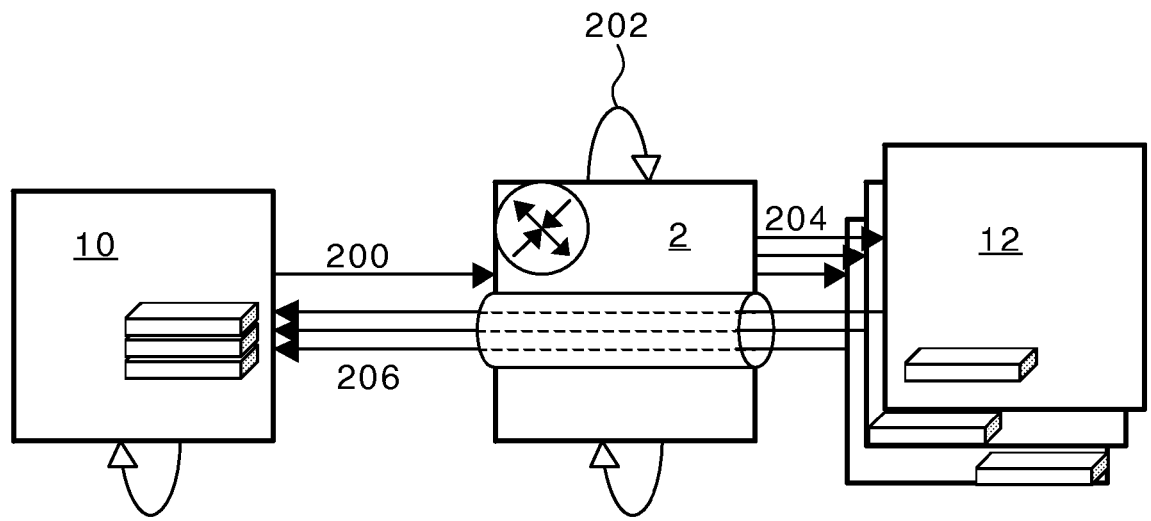
FIG. 3 shows the different steps of a second embodiment of the method according to the present invention.

In a second embodiment of the method, which is shown in FIG. 3, the creation of a first session pseudonym and the formatting of its corresponding inbound identifier arrays are executed already in the requesting server 10. The relayed request, indicated by arrow 200, comprises a reference to the session pseudonym rather than to the local federated identifier of patient P. The inbound identifier array is appended to the request.

The EHR system gateway 2 resolves the inbound identifier array, see arrow 202. Resolving involves extracting the patient identifier for the patient P on the requesting server from the inbound identifier array, looking up the corresponding patient identifier for the providing server, and associating the latter identifier with the session pseudonym, which is also extracted from the inbound identifier array. If there is more than one providing server 12, the gateway 2 creates one additional unique session pseudonym for each additional providing server 12. Prior to relaying, see arrows 204, the request to each providing server 12, the gateway 2 formats one outbound identifier array for each providing server 12 using the patient identifier of the providing server and session pseudonym pair, and appends it to its respective request.

Upon reception of a request, each providing server 12 uses the appended session identifier to resolve the identifier of the patient P in the providing server 12. Furthermore, the providing server 12 retrieves the requested data and sends it to the gateway 2 in a response comprising the session pseudonym replacing all the occurrences of the patient identifier of the providing server with the respective session pseudonym.

The gateway 2 awaits all response data prompted by the original request and aggregates it into one response. It then relays it to the requesting server 10. The requesting server 10 consequently replaces all session pseudonyms with the original identifier before processing the EMR of the patient P, e.g. displaying it to the end-user who originally requested the data.

In a version of this embodiment the gateway appends the inbound identifier array to the response and relays it directly to the requesting server 12, see arrows 206. The requesting server 12 then makes the aggregation.

Figure 4:
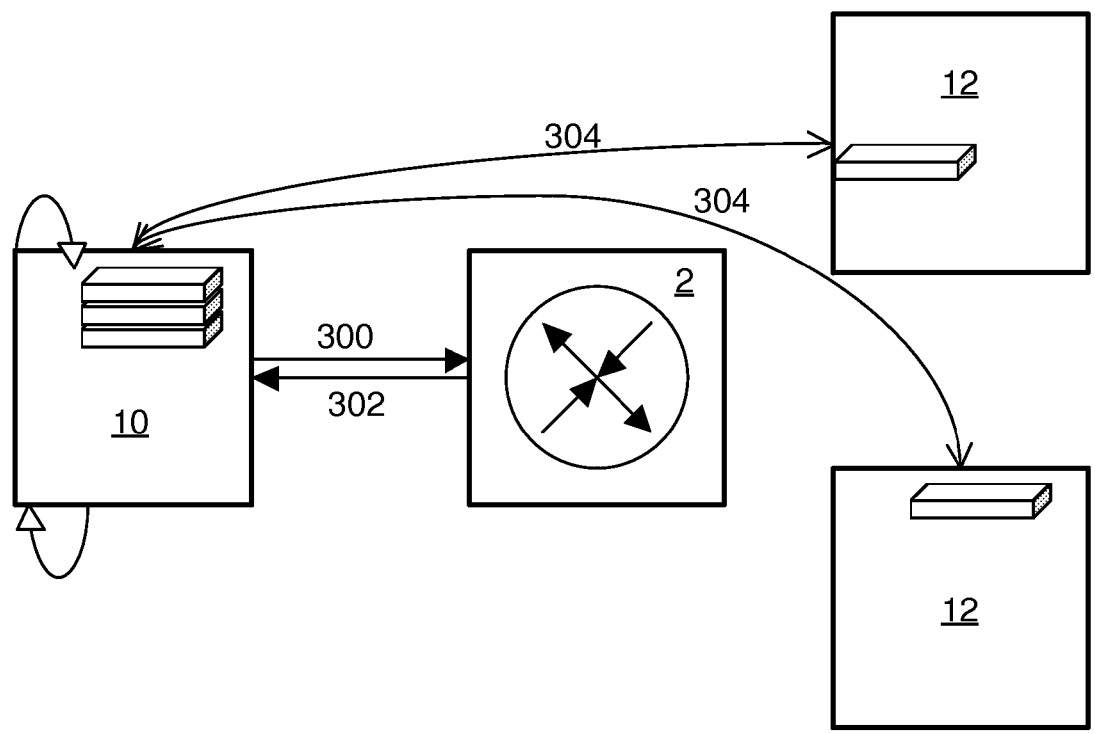
FIG. 4 shows the different step of a third embodiment of the method according to the present invention, in which the requesting server uses a URL to resend the request out-of-band to the providing server.

In a third embodiment, which is shown in FIG. 4, the requesting server sends a request, see arrow 300, to the gateway 2, which resolves the inbound federated identities and for each providing server 12 creates one session pseudonym and encrypts the identifier for patient P in the providing server 12 so that it is only decryptable by its respective providing server 12. Thereafter the gateway 2 returns, see arrow 302, for each providing server 12, one intermediate response comprising the session pseudonym, the identifier for the requesting server 10 itself, the encrypted identifier for the patient P on the providing server 12 and the address, e.g. one uniform resource locator (URL), for each providing server 12.

Upon reception of an intermediate response, the requesting server 10 uses the address(es), e.g. URL(s), to resend, see arrows 304, the request out-of-band to each providing server 12, respectively. The request comprises the session pseudonym and the encrypted identifier for the patient P on the providing server.

Upon reception of an out-of-band request, the providing server, decrypts the encrypted identifier, retrieves the EMR, and sends it as a response with reference to the session pseudonym, directly back to the requesting server 10.

The requesting server 10 consequently replaces all session pseudonyms with the original identifier and aggregates all the EMRs into one EMR before processing the EMR of the patient P, e.g. displaying it to the end-user who originally requested the data.

This embodiment addresses the gateway data bottleneck problem and allows a direct data flow from the requesting server 10 to the providing server 12 without sending the data via the gateway 2, while still preserving privacy.

Figure 5:
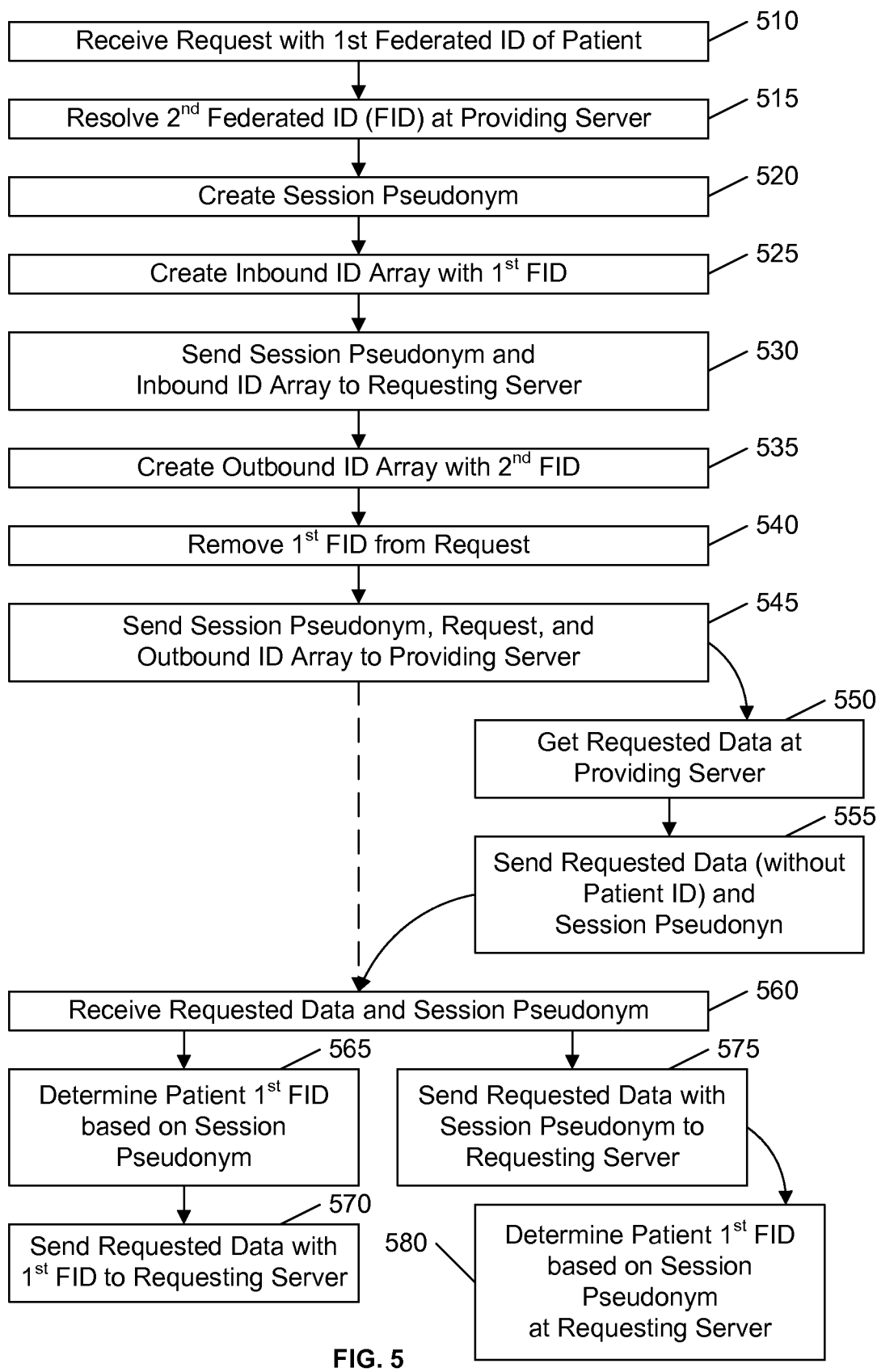
FIG. 5 shows an example flow chart that illustrates a sequence of operations that may be performed in embodiments of this invention.

FIG. 5 shows an example flow chart that illustrates a sequence of operations that may be performed in the above embodiments. In this example, for ease of understanding, a single providing server provides the requested data.

At 510, the request for data for a patient is received at the gateway server; the patient is identified in this request by the federated identifier ($1^{st}$ FID) at the requesting server.

The gateway server resolves the federated identifier ($2^{nd}$ FID) for the patient at the providing server, at 515, and creates a session pseudonym that is linked to these FIDs, at 520. Optionally, the requesting server may have created the session pseudonym and sent it to the gateway server, as disclosed above.

If the requesting server has not provided the session pseudonym, the gateway server may create an inbound ID array that includes the $1^{st}$ FID, at 525, and send it to the requesting server with the session pseudonym, at 530.

At 535, the gateway server creates an outbound ID array that includes the $2^{nd}$ FID; this FID may be encrypted using a key associated with the providing server, as disclosed above. The identifier of the patient ($1^{st}$ FID) is removed from the request for data, at 540, and this request is sent to the providing server along with the outbound ID array and the session pseudonym, at 545.

At the providing server, the providing server obtains the requested data corresponding to the patient identified ($2^{nd}$ FID) in the outbound ID array, at 550. This data is sent back to the gateway (or directly to the requesting server) with the session pseudonym, but without an identifier of the patient, at 555

After the requested data and session pseudonym is received at the gateway, at 560, the gateway may determine the patient identifier ($1^{st}$ FID) based on the session pseudonym, at 565, and send the requested data with the $1^{st}$ FID to the requesting server, at 570. Alternatively, the gateway may send the requested data with the session pseudonym, at 575, and the determination of the $1^{st}$ FID corresponding to the session identifier is performed at the requesting server.

It shall be understood that the different servers described above as requesting server and providing server may switch functionality. Thus, in one situation the server may act as a requesting server and in another situation it may act as a providing server, depending on the circumstances. It should also be understood that certain servers may have a gateway functionality, which enables them to act as gateways. A typical server is an EHR server.

Furthermore, it shall be understood that even though the present invention has been described with preferred embodiments having certain features it is obvious to a person skilled in the art that individual features in one embodiment could be combined with other embodiments or other individual features in other embodiments.

Hence, although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method for exchanging data between at least two servers with use of a gateway, wherein each server holds a unique federated identifier, which identifier identifies a single patient and may act as a requesting server or providing server comprising the steps of;

sending an original request requesting data of the patient from the requesting server to the gateway;

resolving federated identifiers related to the patient with use of the gateway;

creating, by the gateway, one session pseudonym for each pair of providing server holding relevant patient data and the requesting server;

formatting an inbound identifier array that includes the federated identifier of the patient at the requesting server and an outbound identifier array that includes the federated identifier of the patient at each providing server for each session pseudonym;

relaying each session pseudonym and the identifier arrays to each server, respectively;

transferring the patient data from the at least one providing server to the requesting server, the patient data including the corresponding session pseudonym, and not including an identifier of the patient; and replacing all session pseudonyms with the identifier of the requesting server for the patient.

2. The method of claim 1, wherein the original request comprises a first federated identifier for the patient.

3. The method of claim 1, wherein the original request comprises a specification of the desired type of patient data.

4. The method of claim 1, wherein the creation of the session pseudonyms is made by the requesting server and the relaying of the identifier arrays is to the providing server and the gateway.

5. The method of claim 1, wherein the relaying includes:
preparing an outbound request for each providing server, appending the outbound identifier array to the request; and
relaying the request to its respective providing server.

6. The method of claim 3, wherein the resolving and relaying includes:
encrypting the federated identifier for each providing server in such a way that it is only decodable by the gateway and the providing server;
preparing an outbound response with reference to the session pseudonym, the requesting server identifier, said encrypted identifier, and the address of each providing server; and
sending the response to the requesting server.

7. The method of claim 6, wherein the requesting server upon reception of a first response resends the request for patient data out-of-band, directly to respective providing server with reference to respective session pseudonym, the requesting server identifier and the encrypted identifier.

8. The method of claim 7, wherein the providing server upon reception of a request resolves the identifier, via the encrypted identifier, retrieves the requested patient data, and sends it in a response with reference to the session pseudonym.

9. The method of claim 1, wherein the requesting and providing servers are constituted by electronic medical record systems.

10. A non-transitory computer readable medium that includes a computer program that, when executed by a processor, causes the processor to:
receive a first request that requests data of a patient who is identified by a first federated identifier at a requesting server,
resolve a second federated identifier related to the patient at a providing server,
create a session pseudonym corresponding to the requesting and providing servers,
create an outbound identifier array that includes the second federated identifier,
form a second request by removing the first federated identifier from the first request,
send the session pseudonym, the outbound identifier array, and the second request to the providing server, and
receive the requested data of the patient from the providing server in a message that includes the session pseudonym and does not include an identifier of the patient.

11. The medium of claim 10, wherein the program causes the processor to:
create an inbound identifier array that includes the first federated identifier; and
send the session pseudonym, the inbound identifier array, and the requested data to the requesting server.

12. The medium of claim 10, wherein the program causes the processor to:
create a response by adding the first federated identifier of the patent to the received data, based on the session pseudonym; and
send the response to the requesting server.

13. The medium of claim 10, wherein the program causes the processor to:
resolve a third federated identifier related to the patient at an other providing server,
create an other session pseudonym corresponding to the requesting server and the other server,
create an outbound identifier array that includes the third federated identifier,
form a third request by removing the first federated identifier from the first request,
send the other session pseudonym, the other outbound identifier array, and the third request to the other providing server, and
receive the requested data of the patient from the other providing server in an other message that includes the other session pseudonym and does not include an identifier of the patient.

14. The medium of claim 10, wherein the program causes the processor to:
create a response by adding the first federated identifier of the patent to data received from the providing server and the other providing server, based on the session pseudonym and the other session pseudonym, and
send the response to the requesting server.

15. The medium of claim 10, wherein the outbound identifier array includes the second federated identifier in an encrypted form that is able to be decrypted by the providing server.

16. A non-transitory computer readable medium that includes a computer program that, when executed by a processor, causes the processor to:
receive an inbound identifier array, a session pseudonym, and a request for data of a patient from a requesting server,
determine a first federated identifier from the inbound identifier array, and a second federated identifier of the patient at a providing server,
create an outbound identifier array that includes the second federated identifier,
send the outbound identifier array, the session pseudonym, and the request for data to the providing server, and
receive the requested data of the patient from the providing server in a message that includes the session pseudonym and does not include an identifier of the patient.

17. The medium of claim 16, wherein the program causes the processor to:
resolve a third federated identifier related to the patient at an other providing server,
create an other session pseudonym corresponding to the requesting server and the other server,
create an other outbound identifier array that includes the third federated identifier,
send the other session pseudonym, the other outbound identifier array, and at least a portion of the request to the other providing server, and receive the other requested data of the patient from the other providing server in an other message that includes the other session pseudonym and does not include an identifier of the patient.

18. The medium of claim 17, wherein the program causes the processor to:
consolidate the data from the providing server and the other data from the other providing server, and
send the session pseudonym and the consolidated data to the requesting server.

19. The medium of claim 17, wherein the request for data does not include an identifier of the patient.

20. A non-transitory computer readable medium that includes a computer program that, when executed by a processor, causes the processor to:
create an inbound identifier array that includes a first federated identifier of a patient,
create a session pseudonym corresponding to a requesting server,
creating a request that requests data of the patient in a message that includes the session pseudonym and does not include an identifier of the patient,
sending the inbound identifier array and the request to a gateway server,
receive the requested data of the patient from a providing server in a message that includes the session pseudonym and does not include an identifier of the patient, and
determine the identifier of the patient based on the session pseudonym.

* * * * *